(12) United States Patent
Mao et al.

(10) Patent No.: US 11,746,108 B1
(45) Date of Patent: Sep. 5, 2023

(54) TRIAZOLOPYRIDINE POLYMORPH A

(71) Applicant: APM THERAPEUTICS 1, INC., Pittsburgh, PA (US)

(72) Inventors: Jianmin Mao, Winchester, MA (US); Bridget M. Cole, Quincy, MA (US)

(73) Assignee: APM Therapeutics 1, Inc., Pittsburgh, PA (US)

( * ) Notice: Subject to any disclaimer, the term of this patent is extended or adjusted under 35 U.S.C. 154(b) by 0 days.

(21) Appl. No.: 17/838,838

(22) Filed: Jun. 13, 2022

(51) Int. Cl.
 *C07D 471/04* (2006.01)
(52) U.S. Cl.
 CPC ........ *C07D 471/04* (2013.01); *C07B 2200/13* (2013.01)

(58) Field of Classification Search
 CPC .......................... C07D 471/04; C07B 2200/13
 See application file for complete search history.

(56) References Cited

U.S. PATENT DOCUMENTS 10,472,357 B2 * 11/2019 Cole .................... C07D 487/04

* cited by examiner

*Primary Examiner* — Timothy R Rozof
(74) *Attorney, Agent, or Firm* — ELMORE PATENT LAW GROUP, P.C.; Carolyn S. Elmore

(57) ABSTRACT

The invention relates to a Form A polymorph of a triazolopyridine compound, pharmaceutical compositions and methods of use thereof.

10 Claims, 1 Drawing Sheet

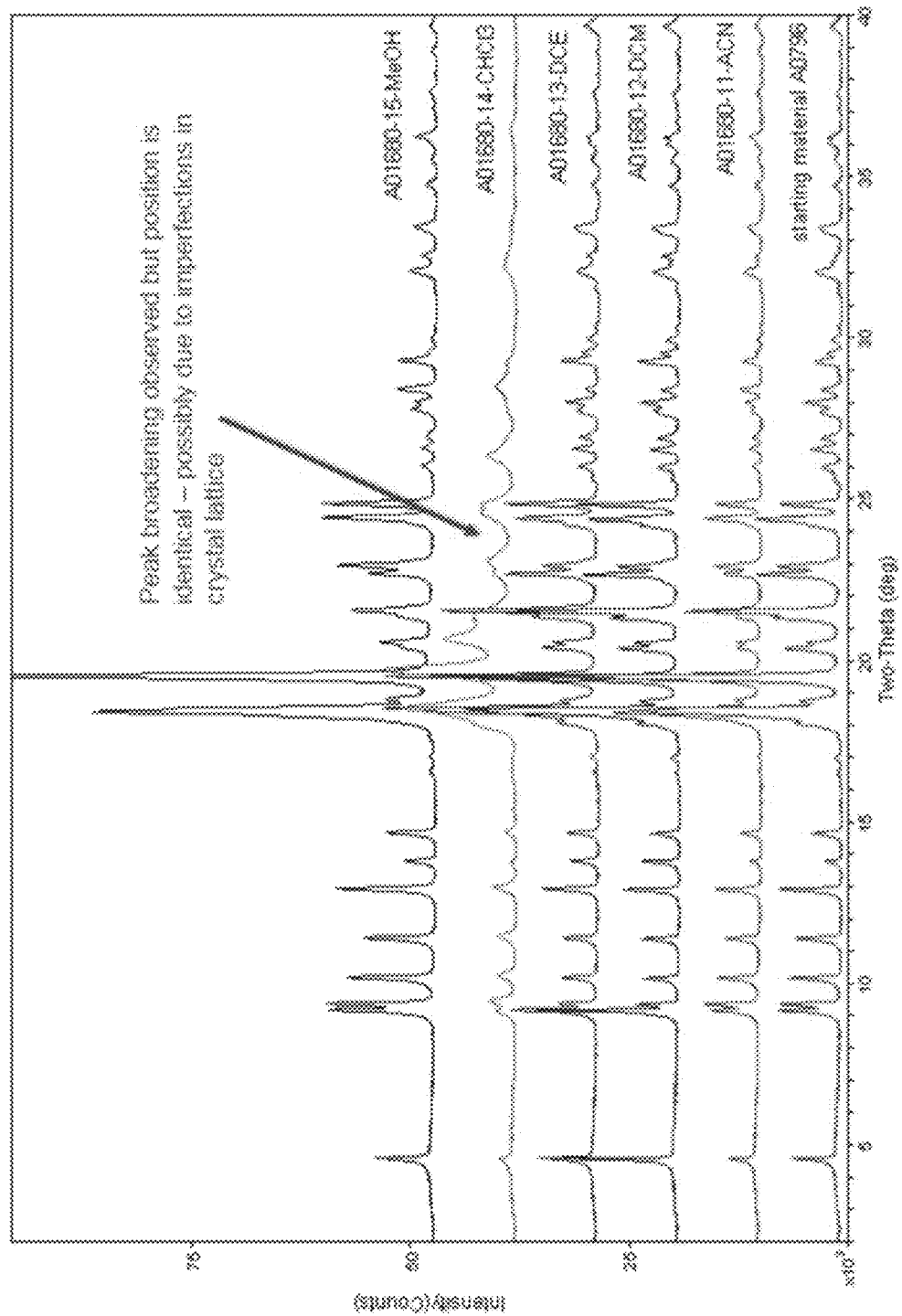

TRIAZOLOPYRIDINE POLYMORPH A

BACKGROUND

Mutations in the CFTR (cystic fibrosis transmembrane conductance regulator) gene result in absence or dysfunction of the protein that regulates ion transport across the apical membrane at the surface of certain epithelia. Although CFTR functions mainly as a chloride channel, it has many other roles, including inhibition of sodium transport through the epithelial sodium channel, regulation of the outwardly rectifying chloride channel, ATP channels, intracellular vesicle transport, and inhibition of endogenous calcium-activated chloride channels. CFTR is also a bicarbonate channel with some conformations enhancing bicarbonate conductance. A deficiency in bicarbonate secretion leads to poor solubility and aggregation of luminal mucins in some organs, with the pancreas, sinuses, vas deferens and other tissues dependent on CFTR-mediated bicarbonate secretion. Reductions in CFTR function, including bicarbonate conductance leads to recurrent acute pancreatitis (RAP) or chronic pancreatitis (CP) by one or more mechanisms (LaRusch et al *PLoS Genetics*. 2014;10(7):e1004376). In the lungs, CFTR dysfunction leads to airway surface liquid (ASL) depletion and thickened and viscous mucus that adheres to airway surfaces. The result is decreased mucociliary clearance (MCC) and impaired host defenses. Dehydrated, thickened secretions lead to endobronchial infection with a limited spectrum of distinctive bacteria, mainly *Staphylococcus aureus* and *Pseudomonas aeruginosa*, and an exaggerated inflammatory response leading to development of bronchiectasis and progressive obstructive airways disease. Pulmonary insufficiency is responsible for most CF-related deaths. (Cohen-Cymberknoh, M et al., *Am. J. Respir. Crit. Care Med.* 1463-1471, 2011).

The prognosis for the treatment of cystic fibrosis (CF) and other CFTR-mediated diseases has improved over the last 40 years. This was achieved by improving pancreatic enzyme supplements to replace the loss of exocrine pancreatic function, drugs designed to treat pulmonary infection, reduce inflammation and enhance mucociliary clearance. Currently the therapeutic challenges are to correct the biochemical defect of CF and to identify effective treatments for chronic respiratory infection. (Frerichs C. et al., *Expert Opin Pharmacother.* 10(7), 1191-202, 2009).

SUMMARY

The invention relates to novel solid forms or polymorphs of the Compound and methods of treating CFTR (cystic fibrosis transmembrane conductance regulator) mediated diseases Compound

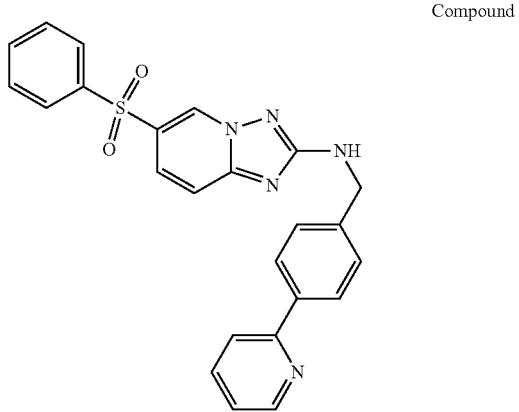 [SMILES: O=S(=O)(c1ccccc1)c1ccc2nc(NCc3ccc(-c4ccccn4)cc3)nn2c1]

In one embodiment, the application provides for crystalline forms of the Compound, such as Form A, characterized by an X-ray powder diffraction (XRPD) comprising one or more peaks at approximately 18.5, 19.5, 21.5, 23, and/or 24 °Θ using CuK α radiation. Form A preferably exhibits a differential scanning calorimetry (DSC) thermogram comprising an endotherm peak which onset at about 203° C.

BRIEF SUMMARY OF THE DRAWING

The FIGURE is an overlay of the XRPD results of Compound Form A as isolated from a number of solvents.

DETAILED DESCRIPTION OF THE INVENTION

The invention relates to stable solid forms or polymorphs of the Compound having the structure:

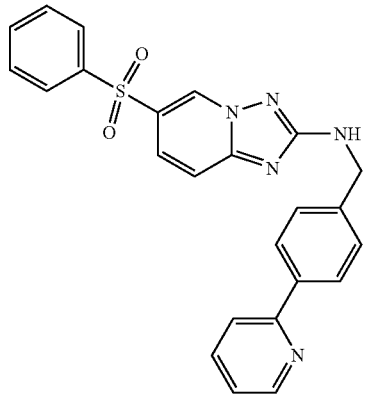 [SMILES: O=S(=O)(c1ccccc1)c1ccc2nc(NCc3ccc(-c4ccccn4)cc3)nn2c1]

The compounds of this invention may be prepared by methods described in U.S. Pat. No. 10,472,357 (Cole et al., granted on Nov. 12, 2019).

Compounds of the invention are useful as modulators of CFTR and treating diseases or disorders mediated by CFTR such as for the treatment of disease, disorders or conditions such as Cystic fibrosis, constipation, distal intestinal obstruction disorder, asthma, sinusitis, sinus obstruction, acute pancreatitis, recurrent acute pancreatitis, chronic pancreatitis, exocrine pancreatic insufficiency, gastrointestinal disorders, liver disorders, biliary disorders, gallbladder disorders, infertility, duodenal inflammation, peptic ulcer disease, Hereditary emphysema, Hereditary hemochromatosis, Coagulation-Fibrinolysis deficiencies, such as Protein C deficiency, Type 1 hereditary angioedema, Lipid processing deficiencies, such as Familial hypercholesterolemia, Type 1 chylomicronemia, Abetalipoproteinemia, Lysosomal storage diseases, such as I-cell disease/Pseudo-Hurler, Mucopolysaccharidoses, Sandhof/Tay-Sachs, Crigler-Najjar type II, Polyendocrinopathy/Hyperinsulemia, Diabetes mellitus, Laron dwarfism, Myleoperoxidase deficiency, Primary hypoparathyroidism, Melanoma, Glycanosis CDG type 1, Hereditary emphysema, Congenital hyperthyroidism, Osteogenesis imperfecta, Hereditary hypofibrinogenemia, ACT deficiency, Diabetes insipidus (DI) Neurophyseal DI, Neprogenic DI, Charcot-Marie Tooth syndrome, Perlizaeus-Merzbacher disease, neurodegenerative diseases such as Alzheimer's disease, Parkinson's disease, Amyotrophic lateral sclerosis, Progressive supranuclear plasy, Pick's disease, several polyglutamine neurological disorders such as Huntington, Spinocerebullar ataxia type I, Spinal and bulbar muscular atrophy, Dentatorubal pallidoluysian, and Myotonic dystrophy, as well as Spongiform encephalopathies, such as Hereditary Creutzfeldt-Jakob disease (due to Prion protein processing defect), Fabry disease and Straussler-Scheinker syndrome.

The compounds of the invention may be administered in combination with antibiotics, anti-inflammatory medicines, bronchodilators, mucus-thinning medicines, proton pump inhibitors, histamine-2 receptor antagonist, pancreatic enzyme replacement therapy. In particular antibiotics for the treatment of bacteria mucoid Pseudomonas may be used in combination with compounds of the invention. Inhaled antibiotics such as tobramycin, colistin, and aztreonam can be used in combination with treatment with compounds of the invention. Anti-inflammatory medicines may also be used in combination with compounds of the invention to treat CFTR related diseases. Bronchodilators can be used in combination with compounds of the invention to treat CFTR related diseases (CFTR-RD).

In one embodiment, the invention relates to combination therapy comprising compounds of the invention and other pharmaceutical agents useful for the treatment of CF and CFTR-RD. In a preferred embodiment, the aminoglycoside gentamicin can be used. In a preferred embodiment, CFTR potentiators, CFTR enhancers or CFTR correctors may be used in combination with compounds of the invention.

In one embodiment, the invention relates to pharmaceutical compositions comprising compounds of the invention and pharmaceutically acceptable carriers. The compositions may include compounds of the invention, and optionally a pharmaceutically acceptable carrier, adjuvant or vehicle. In certain embodiments, these compositions optionally further comprise one or more additional therapeutic agents useful for the treatment of CFTR-related diseases or disorders.

Pharmaceutical Compositions

The pharmaceutical compositions of the present invention comprise a therapeutically effective amount of a compound of the present invention formulated together with one or more pharmaceutically acceptable carriers or excipients.

As used herein, the term "pharmaceutically acceptable carrier or excipient" means a non-toxic, inert solid, semi-solid, gel or liquid filler, diluent, encapsulating material or formulation auxiliary of any type. Some examples of materials which can serve as pharmaceutically acceptable carriers are sugars such as lactose, glucose and sucrose; cyclodextrins such as alpha-(α), beta-(β) and gamma-(γ) cyclodextrins; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols such as propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The pharmaceutical compositions of this invention may be administered orally, parenterally, by inhalation spray, topically, rectally, nasally, buccally, vaginally or via an implanted reservoir. In a preferred embodiment, administration is parenteral administration by injection.

The pharmaceutical compositions of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intraarticular, intraarterial, intrasynovial, intrasternal, intrathecal, intralesional and intracranial injection or infusion techniques.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, EtOAc, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions, may be formulated according to the known art using suitable dispersing or wetting agents and suspending agents. The sterile injectable preparation may also be a sterile injectable suspension or emulsion, such as INTRALIPID®, LIPOSYN® or OMEGAVEN®, or solution, in a nontoxic parenterally acceptable diluent or solvent, for example, as a solution in 1,3-butanediol. INTRALIPID® is an intravenous fat emulsion containing 10-30% soybean oil, 1-10% egg yolk phospholipids, 1-10% glycerin and water. LIPOSYN® is also an intravenous fat emulsion containing 2-15% safflower oil, 2-15% soybean oil, 0.5-5% egg phosphatides 1-10% glycerin and water. OMEGAVEN® is an emulsion for infusion containing about 5-25% fish oil, 0.5-10% egg phosphatides, 1-10% glycerin and water. Among the acceptable vehicles and solvents that may be employed are water, Ringer's solution, USP and isotonic sodium chloride solution. In addition, sterile, fixed oils are conventionally employed as a solvent or suspending medium. For this purpose, any bland fixed oil can be employed including synthetic mono—or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or: a) fillers or extenders such as starches, lactose, sucrose, glucose, mannitol, and silicic acid; b) binders such as, for example, carboxymethylcellulose, alginates, gelatin, polyvinylpyrrolidinone, sucrose, and acacia; c) humectants such as glycerol; d) disintegrating agents such as agar-agar, calcium carbonate, potato or tapioca starch, alginic acid, certain silicates, and sodium carbonate; e) solution retarding agents such as paraffin; f) absorption accelerators such as quaternary ammonium compounds; g) wetting agents such as, for example, cetyl alcohol and glycerol monostearate; h) absorbents such as kaolin and bentonite clay; and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

For pulmonary delivery, a therapeutic composition of the invention is formulated and administered to the patient in solid or liquid particulate form by direct administration e.g., inhalation into the respiratory system. Solid or liquid particulate forms of the active compound prepared for practicing the present invention include particles of respirable size: that is, particles of a size sufficiently small to pass through the mouth and larynx upon inhalation and into the bronchi and alveoli of the lungs. Delivery of aerosolized therapeutics is known in the art (see, for example U.S. Pat. No. 5,767,068 to VanDevanter et al., U.S. Pat. No. 5,508,269 to Smith et al., and WO 98/43650 by Montgomery).

The compositions described herein can be formulated in a unit dosage form. The term "unit dosage form" refers to physically discrete units suitable as unitary dosage for subjects undergoing treatment, with each unit containing a predetermined quantity of active material calculated to produce the desired therapeutic effect, optionally in association with a suitable pharmaceutical carrier. The unit dosage form can be for a single daily dose or one of multiple daily doses (e.g., about 1 to 4 or more times per day). When multiple daily doses are used, the unit dosage form can be the same or different for each dose. The amount of the active compound in a unit dosage form will vary depending upon, for example, the host treated, and the particular mode of administration. In one embodiment, the unit dosage form can have one of the compounds of the invention as an active ingredient in an amount of about 10 mg, 20 mg, 30 mg, 40 mg, 50 mg, 100 mg, 150 mg, 200 mg, 250 mg, 300 mg, 400 mg, 500 mg, 600 mg, 700 mg, 750 mg, 800 mg, 900 mg, 1000 mg, or 1,250 mg.

In some embodiments, the compounds of the invention can be administered in a dose of at least about 10 mg/day to at least about 1500 mg/day. In some embodiments, the compounds of the invention are administered in a dose of at least about 300 mg (e.g., at least about 450 mg, at least about 500 mg, at least about 750 mg, at least about 1,000 mg, at least about 1250 mg, or at least about 1500 mg).

Dose adjustments can be made for patients with mild, moderate or severe hepatic impairment (Child-Pugh Class A). Furthermore, dosage adjustments can be made for patients taking one or more Cytochrome P450 inhibitors and inducers, in particular CYP3A4, CYP2D6, CYP2C9, CYP2C19 and CYP2B6 inhibitors and inducers. Dose adjustments can also be made for patients with impaired Cytochrome P450 function such as poor, intermediate, extensive and ultra-rapid metabolizers.

Definitions

Listed below are definitions of various terms used to describe this invention. These definitions apply to the terms as they are used throughout this specification and claims, unless otherwise limited in specific instances, either individually or as part of a larger group.

As used herein, the word "approximately," especially with respect to the XRPD peaks, is intended to refer to a peak lying +/−0.5 of the value provided, when adjusted to be consistent with the XPRD pattern set forth in the Figure.

As used herein, the term "effective amount" of the subject compound, with respect to the subject method of treatment, refers to an amount of the subject compound which, when delivered as part of desired dose regimen, brings about management of the disease or disorder to clinically acceptable standards.

"Treatment" or "treating" refers to an approach for obtaining beneficial or desired clinical results in a patient. For purposes of this invention, beneficial or desired clinical results include, but are not limited to, one or more of the following: alleviation of symptoms, diminishment of extent of a disease, stabilization (i.e., not worsening) of a state of disease, preventing spread (i.e., metastasis) of disease, preventing occurrence or recurrence of disease, delay or slowing of disease progression, amelioration of the disease state, and remission (whether partial or total).

List of Abbreviations:
All temperatures are in degrees Centigrade
CF—cystic fibrosis
CFTR—cystic fibrosis transmembrane conductance regulator
CFTR-RD cystic fibrosis transmembrane conductance regulator related diseases
DIPEA—N,N-diisopropylethylamine
DMF—dimethylformamide
DMSO—dimethylsulfoxide
ENaC—epithelial sodium channel
Et$_2$O—diethyl ether
Et$_3$N—triethylamine
EtOAc—ethyl acetate
h—hours
H$_2$O—water
HATU-(1-[Bis(dimethylamino)methylene]-1H-1,2,3-triazolo[4,5-b]pyridinium 3-oxid hexafluorophosphate)
HBS—Hepes-buffered saline
HCl—hydrochloric acid
HOAc—acetic acid
HPLC—high pressure liquid chromatography
hr—hours
HTS—high throughput screen
MDC—methylenedichloride
Na$_2$SO$_4$—sodium sulfate
NaH—sodium hydride
NaHCO$_3$—sodium bicarbonate
NAUC—normalized area under the curve
NH$_4$Cl—ammonium chloride
NMR—nuclear magnetic resonance
PBS—Phosphate buffered saline
POCl—phosphorus oxychloride
rt—room temperature
TEA—triethylamine
TFA—trifluoroacetic acid
Tetrakis—triphenylphosphine)palladium(0)
THF—tetrahydrofuran
YFP—yellow fluorescent protein

EXAMPLES

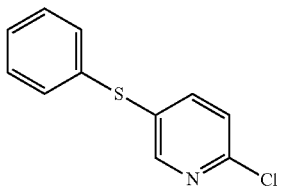 [SMILES: Clc1ccc(Sc2ccccc2)cn1]

2-chloro-5-(phenylthio) pyridine: To a stirred solution of methanol (700 mL) was added Na metal (8.06 g, 350 mmol) at 25° C. Once the Na metal dissolved, 2-chloro-5-iodopyridine (70.0 g, 292.34 mmol), benzenethiol (38.64 g, 350.7 mmol) and copper (7.42 g, 116.758 mmol) were added and the mixture was heated at 80° C. for 16 h. The reaction was cooled to 25° C., 1N NaOH (500 mL) was added and the methanol was evaporated. The reaction mixture was diluted with water (500 mL) and the product was extracted into ethyl acetate (2×500 mL). The organic layer was washed with brine (500 mL), dried over anhydrous sodium sulfate and distilled off to obtain crude 2-chloro-5-(phenylthio) pyridine (80.0 g, (221.90 [M+1])) as a liquid which was carried forward to next step without purification.

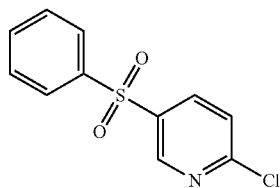 [SMILES: O=S(=O)(c1ccccc1)c1ccc(Cl)nc1]

2-chloro-5-(phenylsulfonyl)pyridine: To a stirred solution of 2-chloro-5-(phenylthio) pyridine (80.0 g, 361.9 mmol) in MDC (500 mL) was added a solution of 60% mCPBA (260.0 g, 904.9 mmol) in MDC (500 mL) drop wise at 0-10° C. The reaction stirred at 25° C. for 2 h. The precipitate was filtered off, and the filtrate was washed with 1N NaOH (500 mL*2) and brine (500 mL), dried over anhydrous sodium sulfate and distilled off. The crude product was purified by column chromatography (20% ethyl acetate in hexane) to obtained 2-chloro-5-(phenylsulfonyl)pyridine (65 g).

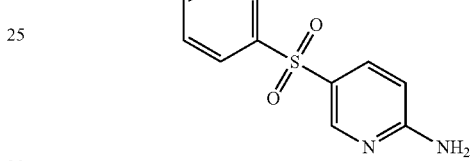

5-(phenylsulfonyl)pyridin-2-amine: A solution of 2-chloro-5-(phenylsulfonyl)pyridine (65.0 g, 256.9 mmol) in Aq.ammonia (650 mL) was stirred at 100° C. in autoclave for 16 h. The reaction mixture cooled to 25° C. and was diluted with water (1000 mL). The solid was filtered and dried under vacuum to obtained 5-(phenylsulfonyl)pyridin-2-amine (52.0 g, 235 [M+1]). 1H NMR: (400 MHz, DMSO) δ: 6.476-6.498(d, J=8.8, 1H), 7.108 (s, 2H), 7.576-7.616 (m, 2H), 7.636-7.675 (m, 1H), 7.754-7.783 (m, 1H), 7.887-7.909 (m, 2H), 8.430-8.436(d, J=2.4, 1H).

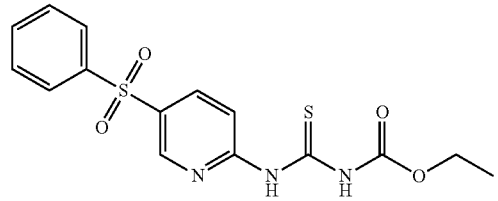 [SMILES: CCOC(=O)NC(=S)Nc1ccc(S(=O)(=O)c2ccccc2)cn1]

Ethyl 1-(carboxamide)-3-(5-(phenylsulfonyl)pyridin-2-yl) thiourea: To a stirred solution of 5-(phenylsulfonyl) pyridin-2-amine (52.0 g, 222.0 mmol) in dioxane (500 mL) was added ethoxycarbonyl isothiocyanate (29.12 g, 222.0 mmol) at 25° C. under nitrogen atmosphere and the resulting reaction mixture was stirred at 25° C. for 16 h. Solvent was distilled off, water (1000 mL) was added and the mixture stirred for 1 h. The solid was filtered and dried under vacuum to obtain the thio-urea derivative (74.0 g, 365.9 [M+1]).

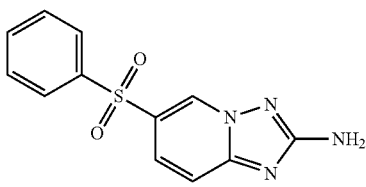 [SMILES: Nc1nc2ccc(S(=O)(=O)c3ccccc3)cn2n1]

6-(phenylsulfonyl)-[1,2,4]triazolo[1,5-a]pyridin-2-amine: To a stirred solution of hydroxylamine hydrochloride (70.44 g, 1013 mmol) in methanol (600 mL) and ethanol (600 mL) was added DIPEA (112.29 mL, 608 mmol) drop wise at 25° C. Next, the thio-urea derivative (74.0 g, 202.7 mmol) was added in one portion at 25° C. and the reaction was stirred for 2 h at 25° C. and then at 60° C. for 16 h. Solvent was distilled off, the reaction mass was diluted with water (1000 mL), and the resulting mixture stirred for 1 h. The solid was filtered and dried under vacuum to obtained 6-(phenylsulfonyl)-[1,2,4]triazolo[1,5-a]pyridin-2-amine (52.0 g, 274.9 [M+]). 1H NMR: (400 MHz, DMSO) δ: 6.539 (s, 2H), 7.460-7.484 (d, J=9.6, 1H), 7.619-7.656 (t, 2H), 7.693-7.729 (m, 1H), 7.757-7.785 (d, J=9.2 1H), 8.043-8.067 (d, J=8.8, 2H), 9.250-9.253 (d, J=1.2, 1H).

2-chloro-6-(phenylsulfonyl)-[1,2,4]triazolo[1,5-a]pyridine: To a stirred solution of 6-(phenylsulfonyl)-[1,2,4]triazolo[1,5-a]pyridin-2-amine (52.0 g, 189.4 mmol) in conc HCl (625 mL) was added copper(II)chloride dihydrate (8.39 g, 49.24 mmol) at 25° C. The reaction mixture was cooled to 0-5° C. and sodium nitrite (15.68 g, 227.0 mmol) in water (293 mL) was added drop wise at 0-5° C. over 30 min and the reaction stirred at 25° C. for 16 h. The reaction mass was diluted with water (3000 mL) and stirred for 1 h. The solid was filtered and dried under vacuum to give crude product which was purified by column chromatography (2% methanol in MDC) to obtained 2-chloro-6-(phenylsulfonyl)-[1,2,4]triazolo[1,5-a]pyridine (44.0 g) 1H NMR: (400 MHz, DMSO) δ: 7.638-7.686(m, 2H), 7.726-7.769(m, 1H), 7.967-8.006(m, 1H), 8.092-8.125(m, 3H), 9.741(s, 1H).

(N-(4-bromobenzyl)-6-(phenylsulfonyl)-[1,2,4]triazolo[1,5-a]pyridin-2-amine: A stirred solution of 2-chloro-6-(phenylsulfonyl)-[1,2,4]triazolo[1,5-a]pyridine (40.0 g, 136.1 mmol) in (4-bromophenyl)methanamine (40 g, 214.9 mmol) was heated at 140° C. for 16 h. The reaction mixture was cooled, diluted with methanol and stirred for 1 h. The solid was filtered and dried under vacuum to obtained (N-(4-bromobenzyl)-6-(phenylsulfonyl)-[1,2,4]triazolo[1,5-a]pyridin-2-amine (38.0 g, 444.9 [M+1]) 1H NMR:(400 MHz, DMSO) δ: 4.437-4.453(d, J=6.4, 2H), 7.286-7.307(d, J=8.4, 2H), 7.482-7.520(m, 3H), 7.611-7.649(t, 2H), 7.688-7.738 (q, 2H), 7.783-7.811(d, J=9.2, 1H), 8.042-8.063(d, J=8.4, 2H), 9.287-9.290(d, J=1.2, 1H).

6-(phenylsulfonyl)-N-(4-(pyridin-2-yl)phenyl)-[1,2,4]triazolo[1,5-a]pyridin-2-amine: Prepared a solution of 6-(phenylsulfonyl)-[1,2,4]triazolo[1,5-a]pyridin-2-amine (300 mg, 1.09 mmol), 2-(4-bromophenyl)pyridine (304 mg, 1.31 mmol), davephos (68 mg, 0.17 mmol) and $Cs_2CO_3$ (708 mg, 2.18 mmol) in dry 1, 4 Dioxane (15 mL). The reaction was degassed under nitrogen and vacuum for 10 minutes. $Pd(OAc)_2$ (39 mg, 0.17 mmol) was added and the reaction mixture was then heated to 90° C. for 16 h. The reaction mixture was cool, diluted with water (50 mL) and extracted with EtOAc (50 mL×2). The organic layer was washed with brine (30 mL), dried over anhydrous sodium sulfate and evaporated to dryness to give crude product which was purified by Flash chromatography (0-5% MDC in methanol) to give pure 6-(phenylsulfonyl)-N-(4-(pyridin-2-yl)phenyl)-[1,2,4]triazolo[1,5-a]pyridin-2-amine (10 mg, 428.09 [M+H]). $^1$H NMR: (400 MHz, DMSO) (3716) δ: 7.27-7.30 (m, 1H), 7.66-7.68 (m, 2H), 7.71-7.75 (m, 3H), 7.81-7.86 (m, 2H), 7.91-7.95 (m, 2H), 8.06-8.12 (m, 4H), 8.62-8.63 (d, 1H), 9.545-9.548 (d, j=1.2Hz, 1H), 10.197 (s, 1H).

An alternative protocol is below:

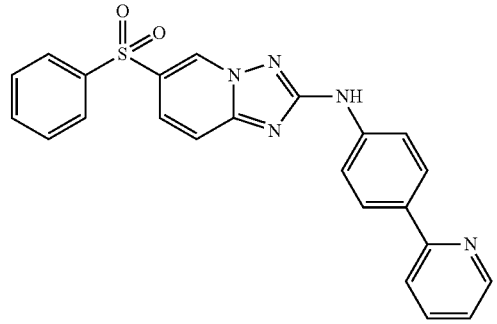 [SMILES: O=S(=O)(c1ccccc1)c1ccc2nc(Nc3ccc(-c4ccccn4)cc3)nn2c1]

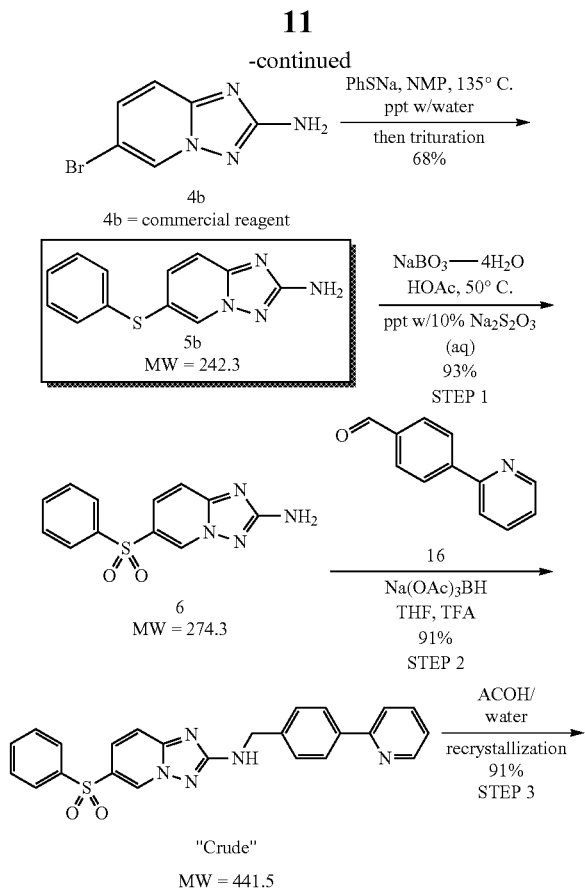

Product

To a round bottom flask, fitted with a mechanical stirrer, condenser, and thermocouple added 6-(phenylthiol)-[1,2,4]triazolo[1,5-a]pyridine-2-amine (150 g, 619 mmol). Acetic acid (10 volumes) was added and heated followed by the addition of NaBO3 (285 g, 1.9 mol) and stirred for 2 h. The reaction was cooled to 35° C. and quenched with 15 volumes of 10% aqueous Na2S2O3. The reaction mixture was filtered through PPFC and Buchner funnel, and dried in the oven until constant mass (153 g, 91% crude yield).

To a round bottom flask equipped with overhead stirrer, condenser, N2 and temperature probe was added 6-(phenylsufonyl)-[1,2,4]triazolo[1,5-a]pyridine-2-amine (153 g, followed by the addition of 4-(pyridine-2-yl)benzaldehyde. The mixture was diluted with 10 volumes of THF followed by the addition of 2,2,2-trifluoroacetic acid (4 equiv). Sodium triacetoxy borohydride was added (1.5 equiv) and stirred overnight at room temperature. Upon completion the reaction was quenched with water (12 volumes) and pH adjusted to 6, using 40% NaOH. The precipitate was filtered, collected, and washed with THF/water mixture twice and then dried in the vacuum oven overnight yielding 216 g (88%) of desired material.

Form A

Form A was examined for solubility by slurring in various organic solvents and solvent mixtures at room temperature and examined by XPRD. Form A was identified in acetone, ethanol, ethylacetate, methanol, water, dichloromethane, and tetrahydrofuran, for example. Saturated solvent-mediated polymorph screen experiments consisted of dissolving Compound at or near reflux in selected organic solvents in order to achieve super-saturation and returning to ambient temperature to facilitate precipitation of solids. Solids were initially examined by PLM and, if birefringent, subsequently examined by FTIR and XRPD for form determination. Birefringent anisotropic needles were formed. The figure provides an overlay of several polymorphs recovered. The bottom line represents the starting material.

Assays for detecting and measuring the effect of compounds on dF508-CFTR channels CFRT-YFP High Throughput Assay:

Corrector Assay:

The following protocol is designed to selectively screen small molecule compounds for F508del other protein-altering genetic variants and wild-type CFTR corrector activities in the HTS YFP flux assay. In this protocol, the cells are incubated with testing compounds for 24 hours, washed with PBS, stimulated with forskolin and a standard potentiator, and read on a 384-well HTS plate reader, such as the Hamamatsu FDDD-6000.

YFP fluorescence intensity is acquired at high speed before and after iodide buffer is injected to the assay cells. Iodide enters the cells via active CFTR channels in the plasma membrane, and quenches the YFP fluorescence. The rate of fluorescence quenching is proportionally related to the total CFTR activities in the cell membrane. dF508-CFTR corrector accelerates YFP quenching by increasing the number of CFTR molecules in the testing cell plasma membrane.

This method was initially developed for bench top plate readers (Galietta, 2001), and was adapted to the HTS format (Sui, 2010).

Fisher Rat Thyroid (FRT) cells stably expressing both human ΔF508-CFTR and a halide-sensitive yellow fluorescent protein (YFP-H148Q/I152L 25, 22) (Galietta, 2001) were cultured on plastic surface in Coon's modified Ham's F12 medium supplemented with FBS 10%, L-glutamine 2 mM, penicillin 100 U/mL, and streptomycin 100 μg/mL. G418 (0.75-1.0 mg/mL) and zeocin (3.2 μg/mL) were used for selection of FRT cells expressing ΔF508-CFTR and YFP. For primary screening, FRT cells were plated into 384-well black wall, transparent bottom microtiter plates (Costar; Corning Inc.) at a cell density of 20,000-40,000 per well. Test compound was applied to the cells at varying concentrations ranging from 2 nM-40 nM in either a 2-fold or 3-fold dilution series. Cells were incubated in a cell culture incubator at 37° C. with 5% CO2 for 24-26 h. Assay plates were washed with DPBS media (Thermo, cat #SH30028.02) to remove unbound cells and compound. Stimulation media (25 μL) containing 20 μM Forskolin & 30 μM P3 [6-(Ethyl-phenyl-sulfonyl)-4-oxo-1, 4-dihydro-quinoline-3-carboxylic acid 2-methoxy-benzylamide] in Hams F-12 coon's modified media was added to the plate wells and incubated at room temperature for 60-120 min. 25 μL of HEPES-PBS-I buffer (10 mM HEPES, 1 mM MgCl2, 3 mM KCl, 1 mM CaCl2, 150 mM NaI) was then added and fluorescence quench curves (Excitation 500 nm/Emission 540 nm; exposure 136 ms) were immediately recorded on an FDSS-6000 plate reader (Hamamatsu). Quench rates were derived from least squares fitting of the data (Sui, 2010).

Potentiator Assay:

The following protocol is designed to selectively screen small molecule compounds for F508del, other protein-altering genetic variants and wild-type CFTR potentiator activities in the HTS YFP flux assay. In this protocol, the cells are incubated at 27° C. for 24 hours with homogeneously boosted dF508-CFTR expression in the cell membrane by the low temperature, washed with PBS, stimulated with forskolin, and read on a 384-well HTS plate reader, such as the Hamamatsu FDDD-6000.

YFP fluorescence intensity is acquired at high speed before and after iodide buffer is injected to the assay cells. Iodide enters the cells via active CFTR channels in the plasma membrane, and quenches the YFP fluorescence. The rate of fluorescence quenching is proportionally related to the total CFTR activities in the cell membrane. dF508del-CFTR potentiators accelerate YFP quenching by increasing CFTR activities in the testing cell plasma membrane.

This method was initially developed for bench top plate readers (Galietta, 2001), and was adapted to the HTS format (Sui, 2010).

Fisher Rat Thyroid (FRT) cells stably expressing both human ΔF508-CFTR and a halide-sensitive yellow fluorescent protein (YFP-H148Q/I152L 25, 22) (Galietta, 2001) were cultured on plastic surface in Coon's modified Ham's F12 medium supplemented with FBS 10%, L-glutamine 2 mM, penicillin 100 U/mL, and streptomycin 100 μg/mL. G418 (0.75-1.0 mg/mL) and zeocin (3.2 μg/mL) were used for selection of FRT cells expressing ΔF508-CFTR and YFP. For primary screening, FRT cells were plated into 384-well black wall, transparent bottom microtiter plates (Costar; Corning Inc.) at a cell density of 20,000-40,000 per well. Cells were incubated in a cell culture incubator at 37° C. with 5% $CO_2$ for 24-26 h. Assay plates were washed with DPBS media (Thermo, cat #SH30028.02) to remove unbound cells. Test compound was applied to the cells at varying concentrations ranging from 2 nM-40 nM in either a 2-fold or 3-fold dilution series in DPBS and stimulated with 20 μM Forskolin (final concentration) in Hams F-12 coon's modified media. Plates were incubated at room temperature for 60-120 min. 25 μL of HEPES-PBS-I buffer (10 mM HEPES, 1 mM $MgCl_2$, 3 mM KCl, 1 mM $CaCl_2$, 150 mM NaI) was then added and fluorescence quench curves (Excitation 500 nm/Emission 540 nm; exposure 136 ms) were immediately recorded on an FDSS-6000 plate reader (Hamamatsu). Quench rates were derived from least squares fitting of the data (Sui, 2010).

References:
Galietta, L. V., Jayaraman, S., and Verkman, A. S. Cell-based assay for high-throughput quantitative screening of CFTR chloride transport agonists. Am. J. Physiol. Cell Physiol. 281(5), C1734-42, 2001.
Sui J., Cotard S., Andersen J., Zhu P., Staunton J., Lee M., Lin S. (2010) Optimization of a Yellow fluorescent protein-based iodide influx high-throughput screening assay for cystic fibrosis transmembrane conductance regulator (CFTR) modulators. Assay Drug Dev. Technol. 2010 December; 8(6): 656-68.

Cell Culture:
Primary CF airway epithelial cells were obtained from the UNC Cystic Fibrosis Tissue Procurement and Cell Culture Core. The cells are grown at 37° C. in a Heracell 150i incubator using growth media (BEGM, Fischer). Cells were then transferred to differentiation media (ALI, UNC) for a minimum of 4 weeks on coated Costar snapwells. Two days before the Ussing assay the mucus on the apical surface of the cells was aspirated after incubating with 200 μL of differentiation Media for at least thirty (30) minutes. One day before the Ussing assay test compounds were added to the basolateral surface of the cells at various test concentrations dissolved in DMSO. The same concentrations of correctors was added to 3 or 4 wells giving a n=3 or n=4 protocol.

Ussing Assay:
Ussing chambers and the associated voltage clamp were obtained from Physiologic Instruments, (San Diego, Calif.). Ussing assays were performed at the 37° C. HEPES buffered physiological saline (HB-PS) was used in apical and basolateral chambers with glucose added to the basolateral solutions. Epithelia were equilibrated for 15 minutes in the chambers while the bath temperature and transepithelial voltage stabilizes adjusts before application of voltage clamp.

Compounds were added in the following order:

| Step | Chamber |
| --- | --- |
| 3.0 μM Benzamil for 20 minutes | apical addition only |
| 10 μM Forskolin for 20 minutes | apical + basolateral addition |
| 10 μM Genestein for 20 minutes | apical + basolateral addition |
| 10 μM CFTR-172 for 20 minutes | apical + basolateral addition |
| 20 μM Bumetanide for 30 minutes | basolateral addition only |

The short circuit current and resistances (typically>300 Ω-cm2) from each chamber was recorded every 10 seconds on stored on a PC using Acquire and Analyze (Physiologic Instruments).

Analysis:
Efficacy of test compounds was compared using the average of the forskolin response and the CFTR-172 response of the test compound divided by the average of the forskolin response and the CFTR-172 elicited by the positive control. Normalized scores were tabulated for all compounds and concentrations. The Compound exhibited an Ec50 between 1-10 μM.

The compounds and processes of the present invention will be better understood in connection with the following examples, which are intended as an illustration only and not limiting of the scope of the invention. Various changes and modifications to the disclosed embodiments will be apparent to those skilled in the art and such changes and modifications including, without limitation, those relating to the chemical structures, substituents, derivatives, formulations and/or methods of the invention may be made without departing from the spirit of the invention and the scope of the appended claims.

The patent and scientific literature referred to herein establishes the knowledge that is available to those with skill in the art. All United States patents and published or unpublished U.S. patent applications cited herein are incorporated by reference. All published foreign patents and patent applications cited herein are hereby incorporated by reference. All other published references, documents, manuscripts and scientific literature cited herein are hereby incorporated by reference.

What is claimed:
1. A Form A polymorph of Compound:

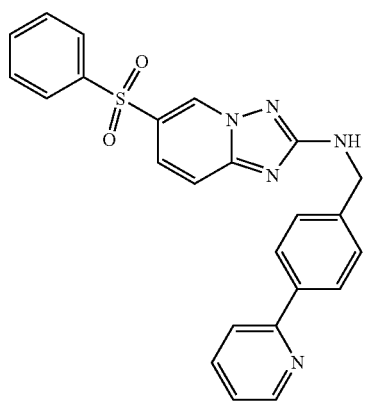 [SMILES: O=S(=O)(c1ccccc1)c1ccc2nc(NCc3ccc(-c4ccccn4)cc3)nn2c1]

characterized by having three or more X-ray powder diffraction peaks at approximately 18.5, 19.5, 21.5, 23, and/or 24 °Θ using CuK α radiation.

2. The Form A polymorph of claim 1 characterized by four or more X-ray powder diffraction peaks at approximately 18.5, 19.5, 21.5, 23, and/or 24 °Θ using CuK α radiation.

3. The Form A polymorph of claim 1 characterized by X-ray powder diffraction peaks at approximately 18.5, 19.5, 21.5, 23, and 24 °Θ using CuK α radiation.

4. The Form A polymorph of claim 1 that exhibits a differential scanning calorimetry (DSC) thermogram comprising an endotherm peak which onset at about 203° C.

5. A pharmaceutical composition comprising a compound according to claim 1 and one or more of a pharmaceutically acceptable carrier, a pharmaceutically acceptable diluent, a pharmaceutically acceptable vehicle, or pharmaceutically acceptable excipient.

6. A method of treating a disease or disorder mediated by cystic fibrosis transmembrane conductance regulator (CFTR) comprising the step of administering a therapeutically effective amount of a compound according to claim 1, wherein said disease or disorder is selected from cystic fibrosis, hereditary emphysema, distal intestinal obstruction disorder, asthma, sinusitis, sinus obstruction, acute pancreatitis, recurrent acute pancreatitis, chronic pancreatitis, exocrine pancreatic insufficiency, gastrointestinal disorders, liver disorders, biliary disorders, gallbladder disorders, infertility, duodenal inflammation, peptic ulcer disease, hereditary hemochromatosis, constipation, coagulation-fibrinolysis deficiencies, type 1 hereditary angioedema, lipid processing deficiencies, familial hypercholesterolemia, type 1 chylomicronemia, abetalipoproteinemia, lysosomal storage diseases, I-cell disease/pseudo-hurler, mucopolysaccharidoses, sandhof/Tay-Sachs, Crigler-Najjar type II, polyendocrinopathy/hyperinsulemia, diabetes mellitus, laron dwarfism, myleoperoxidase deficiency, primary hypoparathyroidism, melanoma, glycanosis CDG type 1, hereditary emphysema, congenital hyperthyroidism, osteogenesis imperfecta, hereditary hypofibrinogenemia, ACT deficiency, diabetes insipidus (DI), neurophyseal DI, neprogenic DI, Charcot-Marie tooth syndrome, perlizaeus-merzbacher disease, neurodegenerative diseases, Alzheimer's disease, Parkinson's disease, amyotrophic lateral sclerosis, progressive supranuclear plasy, Pick's disease, several polyglutamine neurological disorders, spongiform and myotonic dystrophy.

7. A method for treating cystic fibrosis or a symptom thereof, comprising the step of administering to a subject in need thereof a therapeutically effective amount of a compound according to claim 1.

8. A method for treating pancreatitis or a symptom thereof, comprising the step of administering to a subject in need thereof a therapeutically effective amount of a compound according to claim 1.

9. A method for treating liver, biliary or gallbladder disease, dysfunction or a symptom thereof, comprising the step of administering to a subject in need thereof a therapeutically effective amount of a compound according to claim 1.

10. A method for treating intestinal disease, dysfunction or a symptom thereof, comprising the step of administering to a subject in need thereof a therapeutically effective amount of a compound according to claim 1.

* * * * *